United States Patent

Corcoran et al.

[11] Patent Number: 5,981,750
[45] Date of Patent: *Nov. 9, 1999

[54] SOLID-PHASE SYNTHESIS OF CODEINE FROM MORPHINE

[75] Inventors: Robert C. Corcoran, Laramie, Wyo.; Junning Ma, North Wales, Pa.

[73] Assignee: The Board of Regents of the University and Community College System of Nevada, Reno, Nev.

[ * ] Notice: This patent issued on a continued prosecution application filed under 37 CFR 1.53(d), and is subject to the twenty year patent term provisions of 35 U.S.C. 154(a)(2).

[21] Appl. No.: 08/753,040

[22] Filed: Nov. 19, 1996

Related U.S. Application Data

[60] Provisional application No. 60/007,419, Nov. 21, 1995.
[51] Int. Cl.⁶ .......................... C07D 489/02; A61K 31/44
[52] U.S. Cl. ................................. 546/44; 514/282
[58] Field of Search ................................................. 546/44

[56] References Cited

U.S. PATENT DOCUMENTS 4,764,615  8/1988  Ayyangar et al. ..................... 546/44

OTHER PUBLICATIONS

Chemical Abstracts,vol. 93,(11),abst. no. 114,776h,Sep. 15, 1980.
Chemical Abstracts,vol. 109,(5),abst. no. 38,019v,Aug. 01, 1988.
Chemical Abstracts,vol. 112(21),abst.no. 198,876n,May 21,1990.

*Primary Examiner*—Alan L. Rotman
*Attorney, Agent, or Firm*—Morgan, Lewis, & Bockius LLP

[57] ABSTRACT

The specification describes a methylation resin comprising methyl(dialkyl)anilinium salts or methyl(diaryl)anilinium salts covalently bonded to the resin. The methylation resin is used in the solid-phase synthesis of codeine from morphine. Accordingly, the specification describes a process for methylating morphine to form codeine by loading morphine onto a methylation resin comprising methyl(dialkyl) anilinium salts or methyl(diaryl)anilinium salts covalently bonded to the resin; contacting the loaded resin with sufficient hydrocarbon or ether solvent to cover the loaded resin; and heating the loaded resin in the hydrocarbon or ether solvent under sufficient conditions to form codeine. The methylating resin may be used to methylate phenolic moieties on other compounds and to esterify compounds containing carboxylic acid moieties.

13 Claims, 3 Drawing Sheets

PREPARATION OF A POLYMER-SUPPORTED
METHYLATING REAGENT BY COPOLYMERIZATION
AND SUBSEQUENT METHYLATION

PREPARATION OF A POLYMER-SUPPORTED METHYLATING REAGENT BY COPOLYMERIZATION AND SUBSEQUENT METHYLATION

PREPARATION OF A POLYMER-SUPPORTED METHYLATING REAGENT BY STRUCTURAL MODIFICATION OF AN ION-EXCHANGE RESIN

SOLID PHASE METHYLATION OF MORPHINE

SOLID-PHASE SYNTHESIS OF CODEINE FROM MORPHINE

This application claims benefit of provisional application Ser. No. 60/007,419, filed Nov. 21, 1995.

FIELD OF THE INVENTION

This invention relates to a polymeric alkylating reagent and its use in alkylation reactions. In a particular embodiment, this invention relates to a methylation resin and its use in a novel method for synthesizing codeine from morphine.

BACKGROUND

Codeine is widely used as both an analgesic and antitussive drug. Codeine occurs naturally in opium to the extent of 0.3% to 4% depending on the source. Codeine is the methyl ether derivative of morphine, another naturally occurring opiate alkaloid. Morphine is present in opium in the range of 9% to 17% by weight. Although morphine is more abundant and a more potent analgesic drug than codeine, the market demand for codeine far exceeds that for morphine.

Codeine is generally prepared by methylating morphine. A trimethylanilinium salt is generally used as the methylating reagent with the counter anion being ethoxide, chloride or hydroxide. The reaction is generally run in toluene or xylene, and when the counter anion is chloride the reaction must be run in the presence of an organic base, such as sodium ethoxide, to remove the proton from the phenoxy group of morphine. Morphine is usually first dissolved in absolute ethanol and then added to the solution of the methylating reagent in a hydrocarbon solvent. Ethanol is distilled out during the reaction.

The prior art processes require the separation of codeine from the side product of the reaction, N,N-dimethylaniline, which is highly toxic and has been reported to be carcinogenic. This methylating reagent is generally not recycled or reused which increases the cost of the procedure and results in environmental concerns. In addition, both morphine and the organic solvents must be anhydrous which further increases the cost of the process. Both the reaction temperature and the ratio of the reactants also have to be strictly controlled in order to produce high quality codeine in good yield. The prior art processes also consume relatively large amounts of various solvents which are difficult to recycle. Finally, the prior art processes require, at the end of the reaction, that any unreacted morphine be removed from the codeine product.

SUMMARY OF THE INVENTION

The present invention addresses the problems and deficiencies of prior methods to synthesize codeine. In one embodiment the invention relates to a methylation resin comprising methyl(dialkyl)anilinium salts or methyl(diaryl) anilinium salts covalently bonded to the resin. The methylation resin is used in the solid-phase synthesis of codeine from morphine. Accordingly, another embodiment of the invention provides a process for methylating morphine to form codeine by loading morphine onto a methylation resin having methyl(dialkyl)anilinium salts or methyl(diaryl) anilinium salts covalently bonded to the resin; contacting the loaded resin with sufficient hydrocarbon solvent to cover the loaded resin; and heating the loaded resin in the hydrocarbon solvent under sufficient conditions to form codeine. The methylating resin may be used to methylate phenolic moieties on other compounds and to esterify compounds containing carboxylic acid moieties.

DESCRIPTION OF THE INVENTION

Figure 1:
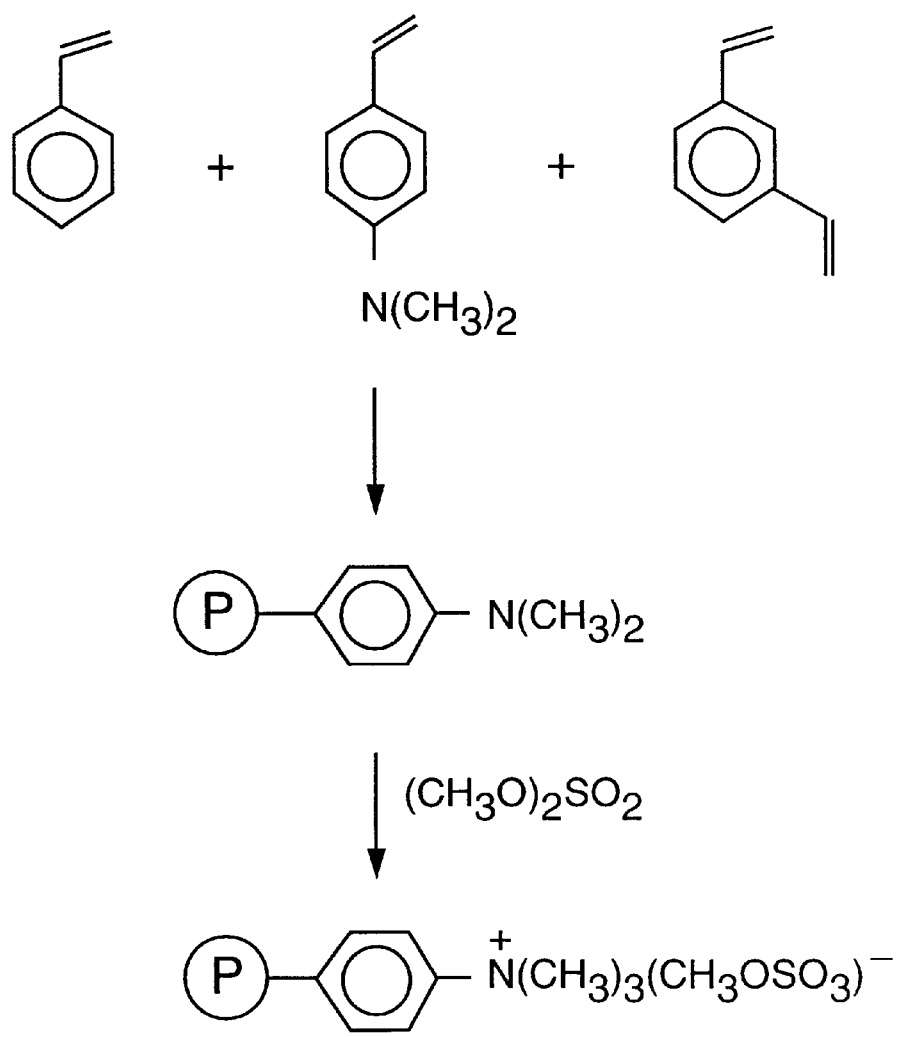
FIG. 1 depicts preparation of a polymer-supported methylating reagent by copolymerization and subsequent methylation.

The present invention provides a process for methylating morphine to form codeine. In the process, morphine is loaded onto a methylation resin having methyl(dialkyl) anilinium or methyl(diaryl) anilinium salts covalently bonded to the resin. The loaded resin is then contacted with sufficient hydrocarbon solvent to cover the loaded resin and then heated in the hydrocarbon solvent under sufficient conditions to form codeine. The codeine may then be recovered from the reaction mixture. While the reaction to form codeine from morphine methylates a phenolic moiety, the methylating resin may also be similarly used to methylate other compounds having a phenolic moiety as well as to esterify carboxylate groups.

According to the present invention, an alkylating agent, preferably a methylating reagent, such as a methyl(dialkyl) anilinium or methyl(diaryl) anilinium salt, is tethered to a polymer creating a novel alkylation or methylation resin. The resin is useful in the synthesis of codeine from morphine. An advantage of this approach is the ability to easily separate the product codeine from side products of the reaction, N,N-dimethyl aniline for example, which remains tethered to the solid support. Another advantage is that since the N,N-dimethyl aniline is not free in solution, this toxic byproduct no longer requires special handling. An additional advantage is the ease in which the resin is recycled without significant loss of efficiency. Yet another advantage, is that methanol is the preferred organic solvent used in this process and is relatively inexpensive and easy to recycle. Finally, much less solvent, for example toluene, is required for this solid phase process as opposed to other known methylation reactions of this type.

According to this invention, the functional methylating reagent is covalently attached to a resin. The methylations agent may be a methyl(dialkyl)anilinium salt or a methyl (diaryl)anilinium salt, such as a trimethylanilinium salt or 3-alkoxytrimethylanilinium (also known as a 3-alkoxytrimethylammonium salt). The resin is preferably a crosslinked resin, which can be either a polystyrene or other polymeric resin. If present, the number of hydroxyl groups in the resin should not be so high as to interfere with the methylating reagent.

As mentioned above, the methylating reagent may be a methyl(dialkyl)anilinium salt or a methyl(diaryl)anilinium salt, preferably a methyl(di-$C_1$–$C_4$-alkyl)anilinium salt or methyl(diphenyl)anilinium salt. The alkyl groups, here and throughout the specification, may be straight or branched alkyl groups. The aryl groups and the aromatic anilinium group may be substituted or unsubstituted. Substitution with electron withdrawing groups that enhance the methylating activity of the reagent is preferred. Particularly preferred methylating reagents include a trimethylanilinium salt or a 3-alkoxytrimethylanilinium salt. The counter ion for the methyl(dialkyl)anilinium or methyl(diaryl)anilinium ion is preferably an alkoxide or hydroxide. Methoxide and hydroxide are preferred counter ions. Other counter ions, such as carboxylate, may also be used.

Morphine is loaded onto the methylating resin by means of a neutralization or anion exchange reaction. Preferably, the resin is in its hydroxide or methoxide form. The morphine is generally loaded using a solution of morphine in a solvent, preferably an alcohol, and most preferably methanol. To produce codeine, the morphine loaded methylating resin is then heated in a hydrocarbon or ether solvent having a boiling point ranging from about 90° to 180° C. Suitable solvents include, for example, benzene-derived solvents, optionally substituted with 1–4 alkyl groups, such as benzene, toluene, or xylene; hydrocarbons such as octane; and ethers such as dibutyl ether. Mixtures of these solvents may also be used.

The codeine product is easily obtained by rinsing the reacted resin thoroughly with a hydrocarbon solvent, such as, for example, toluene. Preferably, the solvent used in the reaction is also used to remove the codeine from the reacted resin. Washing the reacted resin with additional hydrocarbon solvent may recover remaining codeine from the resin. Any washings may then be combined with the reaction solvent recovered from the resin. To yield the codeine, the hydrocarbon solvent may then be removed by means known in the art, preferably by evaporation under reduced pressure. The solvent may be recovered and recycled. Unreacted morphinate is generally retained on the resin and may be recovered by washing with dilute acid in an alcohol, e.g., 5% acetic acid in methanol.

The methylating reagent portion of the resin may also be regenerated by mixing the recovered resin with a methylating agent such as, for example, dimethyl sulfate, chloromethane, bromomethane, or iodomethane. Regeneration can generally be accomplished by contacting the resin with such a methylating agent for one day at room temperature or with moderate heating.

Figure 2:
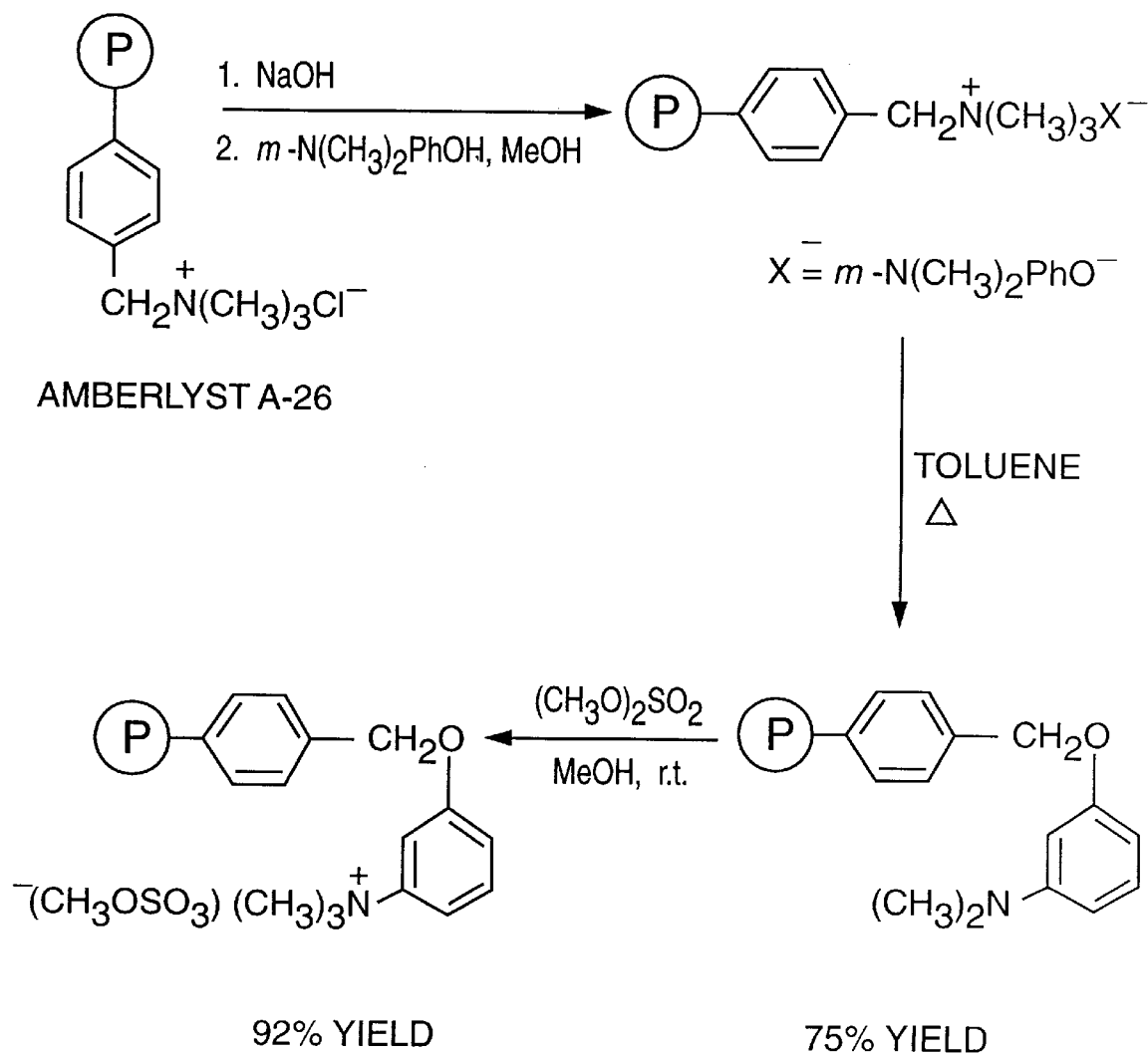
FIG. 2 depicts preparation of a polymer-supported methylating reagent by structural modification of an ion-exchange resin.

A methylation resin of the invention can be prepared by polymerization of styrene and divinyl benzene with 4-dimethylaminostyrene followed by treating the resulting resin with dimethyl sulfate. This is depicted in FIG. 1. Alternatively, a methylation resin of the invention can also be prepared by covalently attaching 3-dimethylaminophenol to Amberlyst A-26 resin, a macroreticular anion exchange resin produced by Rohm and Haas Company, followed by treatment with dimethyl sulfate as described below. This latter resin is inexpensive, behaves well in organic solvents, has good mechanical stability and high functionality. This preparation is shown in FIG. 2. Other types of anion exchange resins containing a methyl(dialkyl)anilinium, a methyl(diaryl)anilinium, or, preferably, a benzyltrimethylanilinium functionality can also be used as starting resins.

In a preferred embodiment, synthesis of a methylation resin from Amberlyst A-26 resin begins by mixing a solution of 3-dimethylaminophenol (DMAP) in methanol with the hydroxide form of the Amberlyst A-26 resin for a period of several hours, preferably 6 to 10 hours. DMAP is loaded quantitatively according to the exchange capacity of the resin. After removal of the excess DMAP solution, the resin is washed with an alcohol, such as methanol, and dried under vacuum. Addition of enough hydrocarbon solvent, preferably toluene, to cover the resin, followed by heating the resin in the hydrocarbon solvent at an elevated temperature, preferably 100° to 115° C., for several hours, preferably 12 to 15 hours, results in the attachment of DMAP covalently to the polymer matrix through an ether linkage. This methodology for attaching a functional group containing moiety to the polymer can be applied to any functionalized phenol.

The modified resin obtained by this procedure is then further methylated with dimethyl sulfate in the presence of a small amount of an alcohol, preferably methanol, at room temperature. The alcohol is used to accelerate the reaction by keeping the resin swelled throughout the reaction.

Figure 3:
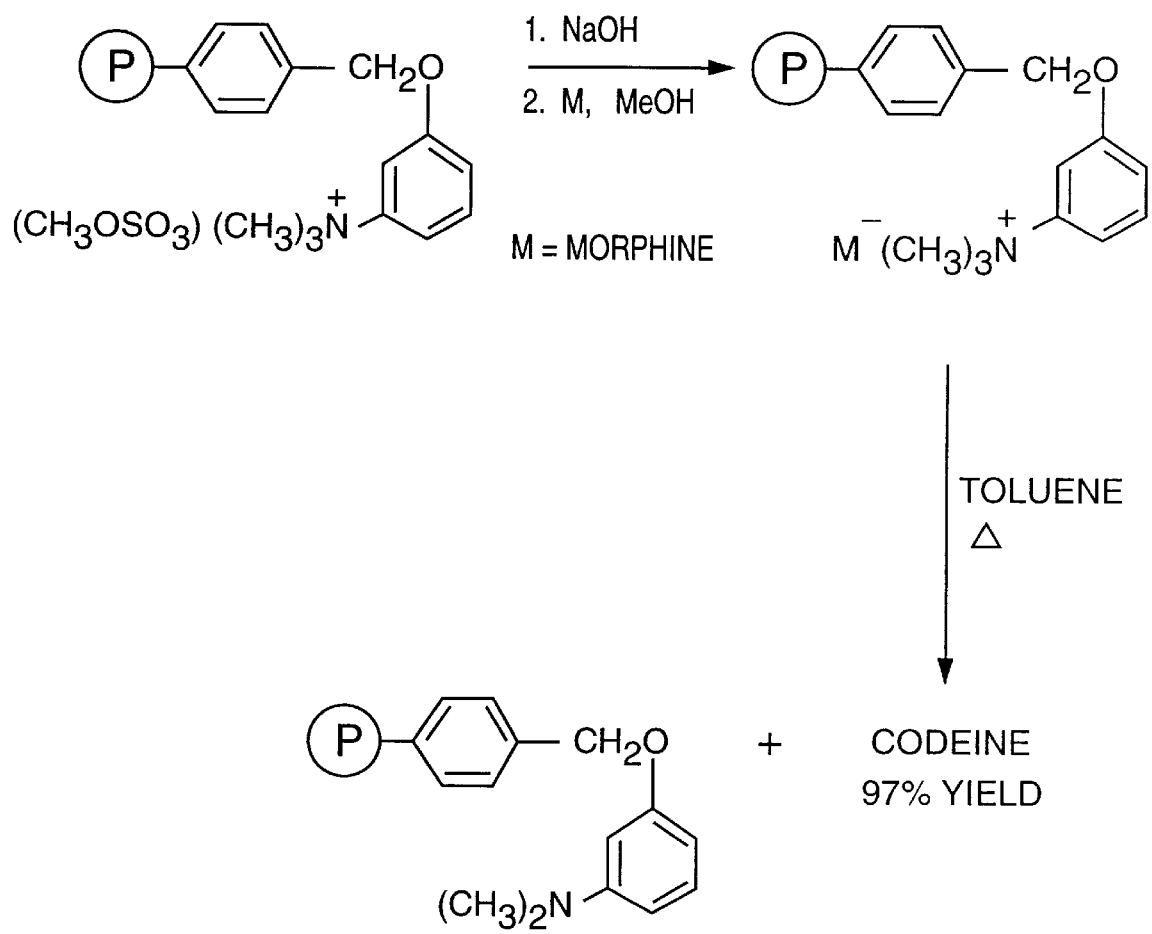
FIG. 3 depicts the solid phase methylation of morphine according to the invention.

The methylation resin thus prepared is initially in the sulfate form and may be converted to the hydroxide form by washing the resin with a basic solution, preferably a sodium hydroxide solution. As depicted in FIG. 3, morphine is then loaded onto the resin in a solvent, preferably methanol, to an extent that is determined by the resin's exchange capacity. After loading, the solvent (i.e., methanol) is substantially, and preferably completely removed, under vacuum or by other known techniques. To form the codeine, the morphine loaded resin is then heated in a hydrocarbon or ether solvent, such as those discussed above, at an elevated temperature, up to the solvent's boiling point. In a preferred embodiment, the morphine loaded resin is heated in toluene at 100° to 105° C., for several hours, preferably 6 to 9 hours, which produces codeine in high yield. The methylation reaction is preferably run, without reflux, in a pressurized, heated container in which stirring and shaking of the resin can be avoided.

The loading capacity of the methylation resin and the purity of the codeine obtained by this procedure depend upon the purity of the morphine which is loaded onto the methylation resin. The greater the purity of morphine, the greater the loading capacity of the methylation resin. The greater the purity of morphine, the greater the purity of the codeine produced by this procedure. However, the codeine produced is always substantially purer than the morphine starting material. Morphine of any purity may be used with the present invention. Generally, the morphine is from 50% to 85% pure. When morphine which is 50% pure is used as the starting material, the codeine produced by this procedure is 75% pure. Codeine produced according to the invention may then be further purified by known techniques, such as recrystallization procedures.

The following example further illustrates this invention, but is not intended to limit the scope of the invention.

EXAMPLE

Amberlyst A-26 resin (20 g) was either obtained in the hydroxide form or converted to the hydroxide form by washing the resin with 1 N NaOH. The resin was washed first with deionized water (50 ml) and then with methanol (30 ml) and mixed with 510 ml of 0.1 M DMAP in methanol. This mixture was allowed to react at room temperature overnight. The resin was then separated from the DMAP solution and washed with 60 ml of methanol. The residual methanol was subsequently removed under vacuum. Toluene was then added in sufficient amounts to cover the resin and this mixture was refluxed at 105° C. for 12 hours. The toluene was drained from the resin and the resin was washed with 60 ml of anhydrous methanol. Enough methanol was added to cover the resin and 20 ml of dimethyl sulfate was then added to the resin in methanol. This mixture was allowed to react at room temperature for 22 hours. The resulting resin was separated from the dimethyl sulfate solution and washed first with methanol and then with deionized water. This methylation resin, containing functional trimethylanilinium groups, was stored in deionized water.

An aliquot of the methylation resin (1.6 ml) in its sulfate form was washed with the following substances in the order listed: 10 ml of 1 M NaCl; 10 ml of deionized water; 40 ml of 1 N NaOH; water until neutral; and 10 ml of methanol. Morphine (11 ml of a 0.1 M solution in methanol) which was 50% pure was mixed with the methylation resin in its hydroxide form for a period of 10 hours. The resin was then separated from the morphine solution and washed with 8 ml of methanol. Residual methanol was removed from the resin under vacuum. Complete removal of methanol before refluxing the loaded resin in toluene is important since the presence of methanol can slow the methylation reaction. Toluene was then added to cover the resin and the mixture was heated at 105° C. for a period of 9 hours. Upon cooling to room temperature, the toluene was separated from the resin and the resin was washed with an additional 10 ml of toluene which was combined with the first toluene fraction. The toluene was evaporated and recycled. The yield of codeine in the residue was determined by High Performance Liquid Chromatography (HPLC) to be 152 mg (98% yield based upon the loading of 145 mg of morphine per gram resin).

The recovered resin was then treated with dimethyl sulfate for one day at room temperature to regenerate the methylation resin. Methylation of morphine with the regenerated methylation resin produced a 97% yield of codeine. The loading capacity of the regenerated resin had not changed and remained at 145 mg of morphine (at 50% purity) per gram of the regenerated methylation resin.

What is claimed is:

1. A process for methylating morphine to form codeine, comprising:

loading morphine onto a methylation resin comprising methyl(dialkyl)anilinium salts or methyl(diaryl) anilinium salts covalently bonded to the resin;

contacting the loaded resin with sufficient hydrocarbon or ether solvent to cover the loaded resin; and heating the loaded resin in the hydrocarbon or ether solvent under sufficient conditions to form codeine.

2. A process of claim 1, wherein the methylating resin contains trimethylanilinium salts covalently bonded to the resin or 3-alkoxytrimethylanilinium salts covalently bonded through an ether linkage to pendent benzyl groups on the resin and the hydrocarbon solvent is toluene.

3. A process of claim 2, wherein the loaded resin in the toluene is heated to 100° to 115° C.

4. A process of claim 1, further comprising the steps of:

recovering the codeine; and regenerating the methylation resin.

5. A process of claim 1, wherein the hydrocarbon or ether solvent is selected from benzene, toluene, xylene, octanes, dibutyl ether and mixtures thereof.

6. A process for methylating a compound having phenolic moiety comprising:

loading a compound having a phenolic moiety onto a methylation resin comprising methyl(dialkyl)anilinium salts or methyl(diaryl)anilinium salts covalently bonded to the resin;

contacting the loaded resin with sufficient hydrocarbon solvent to cover the loaded resin; and heating the loaded resin in the hydrocarbon solvent under sufficient conditions to methylate the phenolic moiety.

7. A process for esterifying a compound having a carboxylic acid moiety, comprising:

loading a compound having a carboxylic acid moiety onto a methylation resin comprising methyl(dialkyl) anilinium salts or methyl(diaryl)anilinium salts covalently bonded to the resin;

contacting the loaded resin with sufficient hydrocarbon or ether solvent to cover the loaded resin; and heating the loaded resin in the hydrocarbon or ether solvent under sufficient conditions to form a methyl ester of the carboxylic acid moiety.

8. A process according to claim 1, wherein the methyl (dialkyl)anilinium salt is a trimethylanilinium salt.

9. A process according to claim 1, wherein the methyl (diaryl)anilinium salt is a methyl(diphenyl)anilinium salt.

10. A process according to claim 6, wherein the methyl (dialkyl)anilinium salt is a trimethylanilinium salt.

11. A process according to claim 6, wherein the methyl (diaryl)anilinium salt is a methyl(diphenyl)anilinium salt.

12. A process according to claim 7, wherein the methyl (dialkyl)anilinium salt is a trimethylanilinium salt.

13. A process according to claim 7, wherein the methyl (diaryl)anilinium salt is a methyl(diphenyl)anilinium salt.

* * * * *